United States Patent

Scovil et al.

[11] Patent Number: 5,160,559
[45] Date of Patent: Nov. 3, 1992

[54] METHOD FOR FORMING A GUIDE CATHETER TIP BOND

[75] Inventors: Brian J. Scovil, New Hope; Henry J. Pepin, Loretto, both of Minn.

[73] Assignee: Scimed Life Systems, Inc., Maple Grove, Minn.

[21] Appl. No.: 606,090

[22] Filed: Oct. 31, 1990

[51] Int. Cl.$^5$ .................... A61M 25/00; B29C 65/02
[52] U.S. Cl. .................. 156/73.6; 156/303.1; 156/304.2; 156/304.6; 264/248; 604/280
[58] Field of Search .............. 156/73.2, 73.6, 303.1, 156/304.2, 304.6, 309.6, 308.4, 309.9, 304.5; 264/248, 23; 604/272, 280, 281, 282

[56] References Cited

U.S. PATENT DOCUMENTS

| | | | |
|---|---|---|---|
| 3,184,353 | 5/1965 | Balamuth et al. | 264/248 |
| 3,860,468 | 1/1975 | Scherer | 156/304.2 |
| 3,985,601 | 10/1976 | Panagrossi | 156/229 |
| 4,003,382 | 1/1977 | Dyke | 128/349 |
| 4,239,575 | 12/1980 | Leatherman | 156/309.6 |
| 4,251,305 | 2/1981 | Becker et al. | 156/86 |
| 4,335,723 | 6/1982 | Patel | 128/349 |
| 4,385,635 | 5/1983 | Ruiz | 128/658 |
| 4,407,691 | 10/1983 | Ishii et al. | 156/304.2 |
| 4,419,095 | 12/1983 | Nebergall et al. | 604/96 |
| 4,531,943 | 7/1985 | Van Tassel et al. | 604/280 |
| 4,551,292 | 11/1985 | Fletcher et al. | 264/139 |
| 4,563,181 | 1/1986 | Wijayarathna et al. | 604/280 |
| 4,636,346 | 1/1987 | Gold et al. | 604/280 |
| 4,661,095 | 4/1987 | Taller et al. | 604/103 |
| 4,790,831 | 12/1988 | Skribiski | 604/282 |
| 4,801,297 | 1/1989 | Mueller | 604/280 |
| 4,842,590 | 6/1989 | Tanabe et al. | 604/282 |
| 4,886,506 | 12/1989 | Lovgren et al. | 604/280 |
| 4,913,701 | 3/1990 | Tower | 604/103 |
| 4,923,659 | 5/1990 | Kunz | 156/304.2 |
| 4,987,018 | 1/1991 | Dickinson et al. | 156/304.2 |
| 5,017,259 | 5/1991 | Kohsai | 156/294 |
| 5,045,072 | 9/1991 | Castillo et al. | 604/280 |

FOREIGN PATENT DOCUMENTS

| | | | |
|---|---|---|---|
| 0334640 | 9/1989 | European Pat. Off. | 604/280 |
| 0405658A2 | 1/1991 | European Pat. Off. | |
| 0749753 | 5/1956 | United Kingdom | 604/280 |

Primary Examiner—Michael W. Ball
Assistant Examiner—Steven D. Maki
Attorney, Agent, or Firm—Kinney & Lange

[57] ABSTRACT

A method for forming a guide catheter with a deformable tip includes setting a mating distal end of a tubular member against a mating proximal end of a soft, deformable tip to form a butt joint. The butt joint is then softened to render the mating proximal and distal ends of the deformable tip and tubular member flowable. The tubular member and the deformable tip are then oscillated along a longitudinal axis such that the materials of the mating proximal and distal ends flow into one another creating a connection zone. The connection zone then solidifies to form a lap joint tip bond that securely fastens the deformable tip to the tubular member.

11 Claims, 4 Drawing Sheets

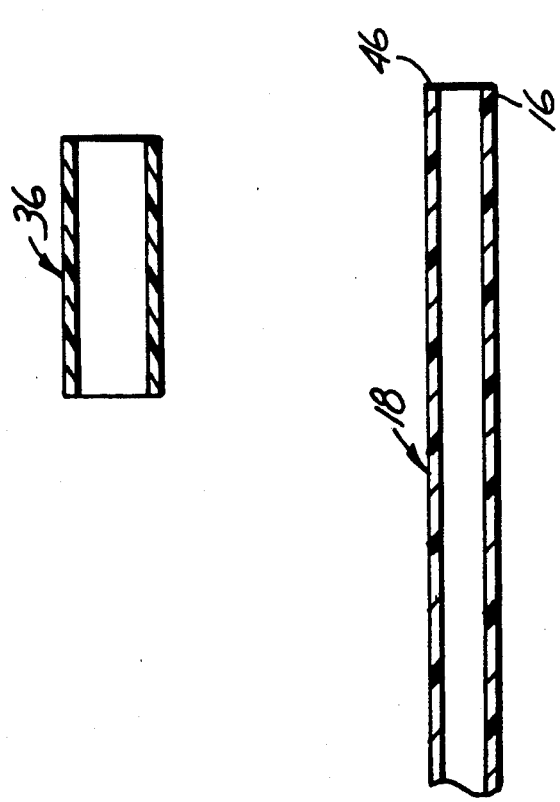

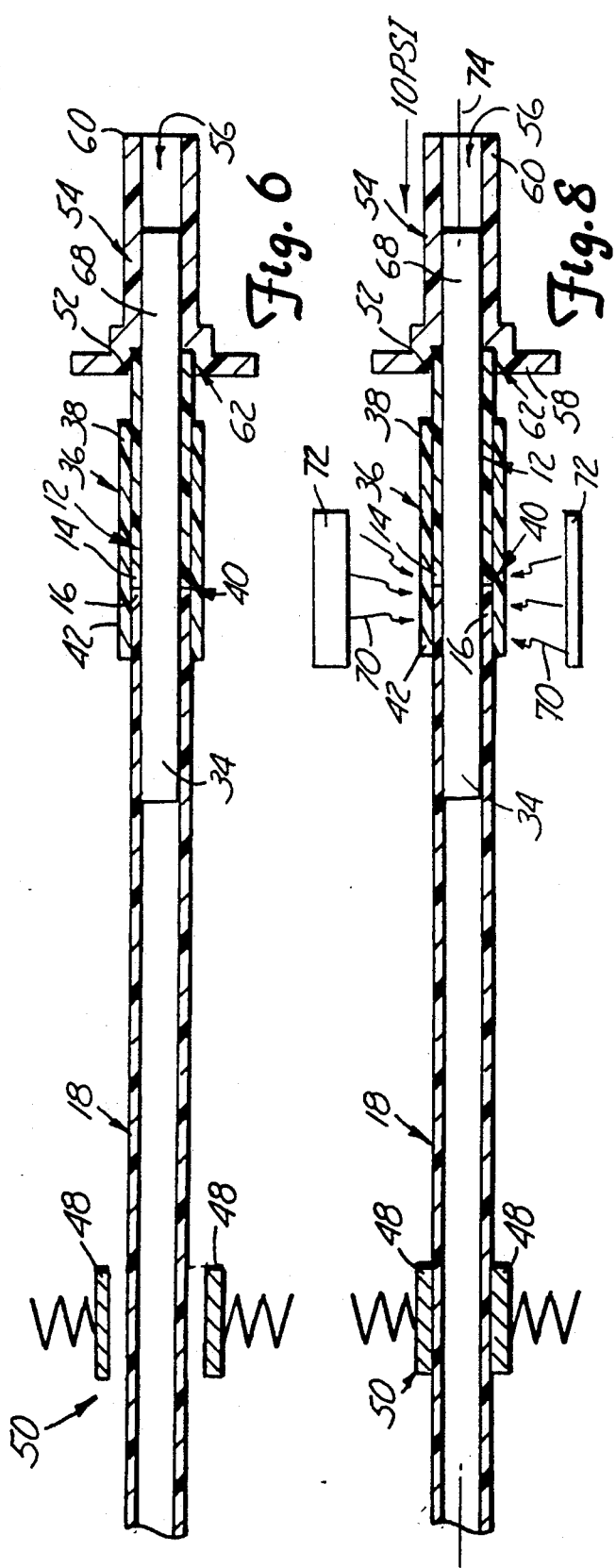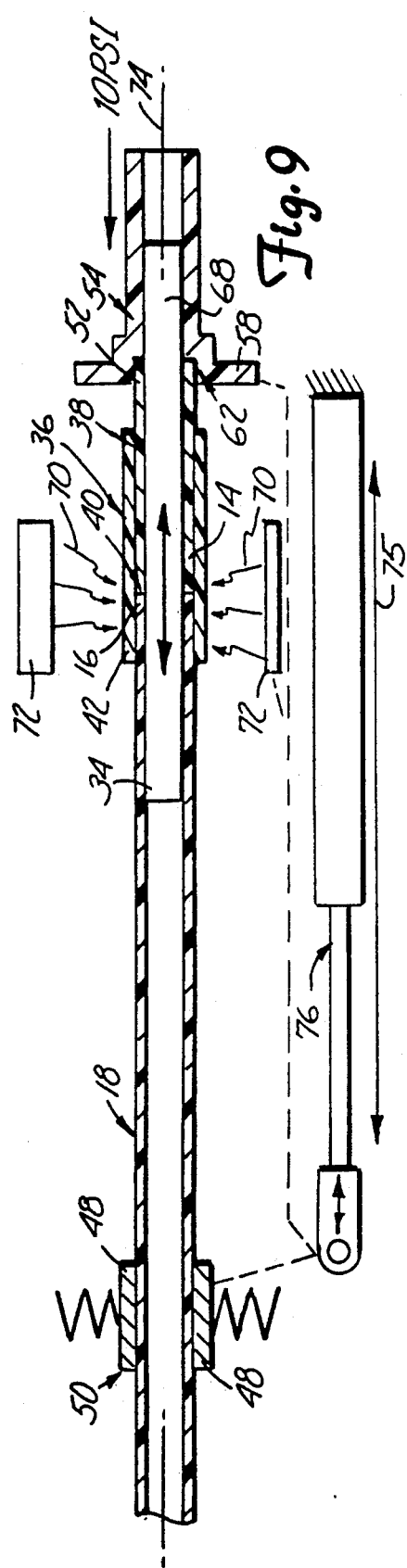

METHOD FOR FORMING A GUIDE CATHETER TIP BOND

BACKGROUND OF THE INVENTION

The present invention relates to the field of angioplasty. In particular, the present invention is a method for forming a guide catheter with a deformable tip.

Angioplasty has gained wide acceptance in recent years as an efficient and effective method for treating various types of vascular diseases. In particular, angioplasty is widely used for opening stenosis in the coronary arteries, although it is also used for treatment of stenosis in other parts of the vascular system.

The most widely used form of angioplasty makes use of a guide catheter positioned within the vascular system of a patient. The distal end of the guide catheter is inserted into the femoral artery located in the groin of the patient and is pushed distally up through the vascular system until the distal end of the guide catheter is located in the ostium of the coronary artery. The proximal end of the guide catheter protrudes outside of the patient's body to provide an entryway for subsequent insertion of additional angioplasty devices. The additional angioplasty devices includes dilatation catheters such as non-over-the-wire and over-the-wire balloon catheters.

Methods for forming catheters having soft, deformable tips are generally known. U.S. Pat. No. 4,551,292 to Fletcher et al. discloses one such method. Catheter stock is first ground down to form a frusto conical end portion. Next, the tapered end of the catheter stock is inserted into a suitable mold and a plastic, that is softer than catheter stock, is added to the mold to create a softer end portion on the catheter stock. The end portion of the catheter is then ground away and a forming tool is used to form a bulbous end on the end portion of the catheter. The resulting connection exhibits very little surface area contact between the catheter stock and the end portion.

It is evident that there is a continuing need for improved methods for forming guide catheters with deformable tips. Specifically, a method for forming a guide catheter with a deformable tip is needed that creates a lap joint tip bond exhibiting a large amount of surface area contact between the mating proximal end of the soft, deformable tip and the mating distal end of the main tubular member that makes up the guide catheter.

SUMMARY OF THE INVENTION

The present invention is a method of coupling a deformable first shaft member to a second shaft member by forming a high surface area connection zone between the first and second members. To form the connection zone, a mating proximal end of the deformable first shaft member is set against a mating distal end of the second shaft member to form a butt joint. The butt joint is then softened to render the mating proximal and distal ends of the first and second shaft members flowable. While the mating ends are in a flowable state, the first and second shaft members are oscillated longitudinally along an axis defined by the longitudinal extent of the first and second shaft members. The oscillating motion causes the mating proximal end and mating distal end to flow into one another, thereby forming a connection zone. The connection zone is then allowed to solidify. This method results in a solidified connection zone with a large amount of surface area contact between the first and second shaft members. This large amount of surface area contact creates a bond that firmly couples the deformable first shaft member to the second shaft member.

In application, the first shaft member is a soft, tubular, deformable tip and the second shaft member is a thermoplastic, tubular member. The method of the present invention is used to secure the deformable tip to the tubular member to form a guide catheter with a deformable tip on its distal end.

In practice, a rigid mandrel is inserted through the deformable tip such that a portion of the mandrel extends past the mating proximal end of the deformable tip. Next, a sleeve member is slid over the tip so that a first section of the sleeve member extends about the mating proximal end. The mating distal end of the tubular member is then set against the proximal end of the deformable tip to thereby form the butt joint. In this position, a second section of the sleeve member extends about the mating distal end of the tubular member, and the portion of the mandrel that extends past the mating proximal end of the tip is received within the mating distal end of the tubular member.

The tubular member is secured by a clamp member against movement relative to the deformable tip and heat from a heat source is applied to the deformable tip and tubular member to soften the mating proximal and distal ends at the butt joint. While heat is applied to the butt joint, the deformable tip is continuously forced against the tubular member by way of a pressure member to maintain contact between the mating proximal and distal ends. Softening of the butt joint renders the mating proximal end of the deformable tip and the mating distal end of the tubular member flowable.

In one embodiment, the butt joint is heated for 45 seconds at a temperature 430° F. while the pressure member maintains 10 p.s.i. of pressure against the deformable tip. The mandrel and the sleeve member prevent the mating proximal and distal ends from bulging radially during softening of the butt joint.

Next, the tubular member and the deformable tip are longitudinally oscillated such that the mating distal and proximal ends flow into one another. In one embodiment, the tubular member and deformable tip are oscillated for a period of three seconds. This procedure causes the formation of a lap joint (i.e., connection zone) wherein the mating proximal end of the deformable tip forms a tapered apex that extends proximally, and wherein the mating distal end of the tubular member forms a V-shaped groove that widens distally.

After the oscillation, the clamp is disengaged from the tubular member, thereby releasing the tubular member and the pressure member is disengaged from the deformable tip, thereby removing the pressure at the tip. The lap joint is then allowed to solidify (i.e., cure) by cooling at room temperature. Alternatively, solidification of the lap joint can be hastened by immersing the lap joint in an alcohol bath or by the use of a circulating air cooler.

This method of forming a guide catheter with a deformable tip is relatively uncomplicated. The method of the present invention produces a lap joint tip bond exhibiting a large amount of surface area contact between the mating distal end of the tubular member and the mating proximal end of the deformable tip that make up the guide catheter. This large amount of surface area contact creates an extremely strong bond.

BRIEF DESCRIPTION OF THE DRAWINGS

FIG. 3 is a diagrammatic sectional view of a mandrel inserted within the deformable tip and a sleeve member with the mandrel shown in full for clarity.

FIG. 4 is a diagrammatic sectional view similar to FIG. 3 showing the sleeve member positioned over the deformable tip and mandrel with a catheter member spaced therefrom.

FIG. 5 is a diagrammatic sectional view similar to FIG. 4 with the catheter member positioned within the sleeve and abutting the deformable tip.

FIG. 6 is a diagrammatic sectional view similar to FIG. 5 with the catheter member positioned within a clamping device and the deformable tip abutting a pressure member.

FIG. 8 is a diagrammatic sectional view similar to FIG. 6 showing the catheter member clamped in position with pressure being applied to the deformable tip by the pressure member and heat being applied to the abutting ends of the catheter member and the deformable tip.

FIG. 9 is a diagrammatic sectional view similar showing oscillation of the arrangement of FIG. 8 in accordance with the method for forming a lap joint tip bond of the present invention.

While the above identified drawing figures set forth a preferred embodiment, other embodiments of the present invention are also contemplated, as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity. In addition, the use of such relational terms as left/right, upper/lower, horizontal/vertical, etc. are used herein for reference purposes only and are not intended to be limiting features of the invention disclosed.

DETAILED DESCRIPTION OF THE PREFERRED EMBODIMENTS

Figure 1:
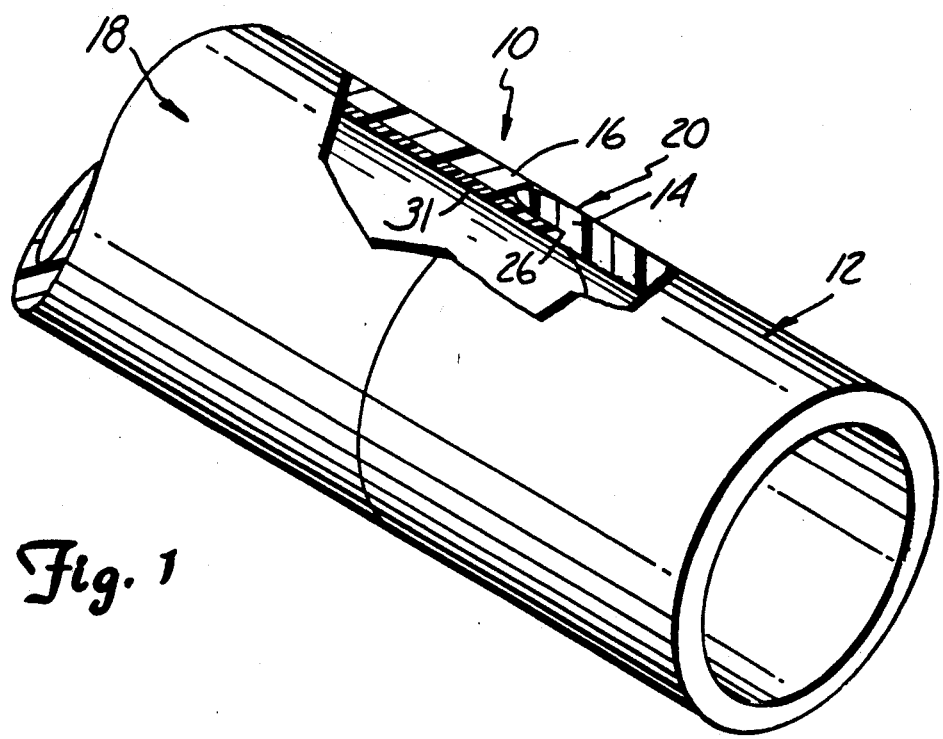
FIG. 1 is a perspective view of a guide catheter with a deformable tip bonded thereto in accordance with the method for forming a lap joint tip bond of the present invention, with some parts broken away to illustrate the lap joint tip bond.
Figure 2:
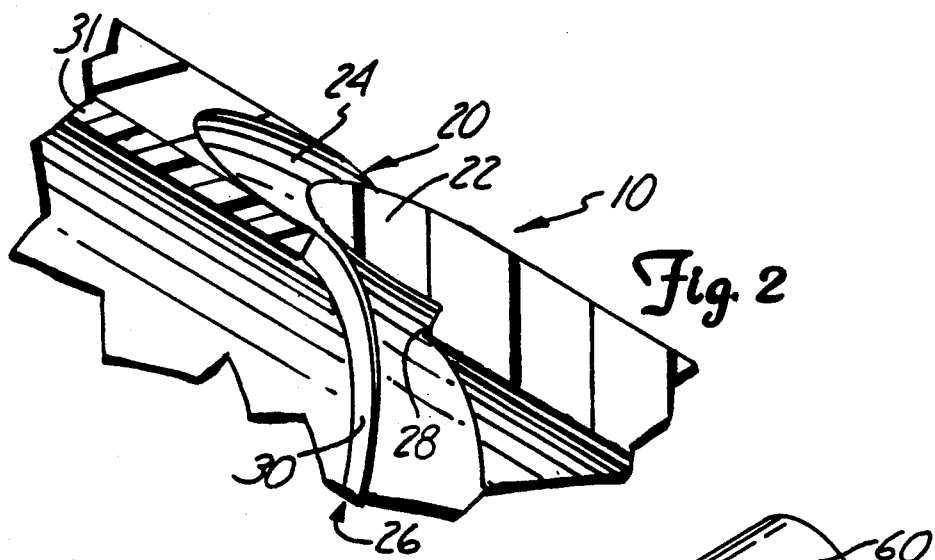
FIG. 2 is a greatly enlarged perspective view of the lap joint tip bond shown in FIG. 1 with the components shown exploded for clarity only.

A distal end of a guide catheter 10 formed in accordance with the method of the present invention is illustrated generally in FIGS. 1 and 2. The guide catheter 10 includes a first shaft member, such as a soft thermoplastic or elastomeric, tubular, deformable tip 12 coupled at its mating proximal end 14 to a mating distal end 16 of a second shaft member, such as a thermoplastic or elastomeric, tubular member 18 (only a portion of which is shown in FIG. 1). The deformable tip 12 is coupled to the tubular member 18 by way of a connection zone, such as a lap joint tip bond 20.

The method of forming a guide catheter with a deformable tip in accordance with the present invention produces the lap joint tip bond 20, wherein the mating proximal end 14 of the deformable tip 12 forms a tapered apex 22 that extends proximally, and the mating distal end 16 of the tubular member 18 forms a V-shaped groove 24 that widens distally (see FIG. 2). A partial butt joint 26 forms between a flat edge portion 28 of the mating proximal end 14 and a flat edge section 30 of the mating distal end 16 due to a coating of lubricous material 31, such as TEFLON, on an inner wall of the tubular member 18. The lap joint tip bond 20 occurs as a blending of the materials from which the deformable tip 12 and tubular member 18 are formed.

The lap joint tip bond 20 as illustrated in FIG. 1 has been formed in accordance with the method of the present invention. FIG. 2 is provided only for clarity and illustrates the lap joint tip bond 20 in an exploded condition. It is to be understood that the shape of the mating proximal 14 of the deformable tip 12 and the shape of the mating distal end 16 of the tubular member 18 shown in FIGS. 1 and 2 is produced only after the method of the present invention has been carried out.

The method for forming the lap joint tip bond 20 is illustrated in FIGS. 3–6, 8 and 9. As shown in FIG. 3, a rigid mandrel 32 is first inserted through the deformable tip 12 such that a first portion 34 of the mandrel 32 extends past the mating proximal end 14 of the deformable tip 12. Next, as seen in FIG. 4, a sleeve member 36 is slid over the deformable tip 12 so that a first section 38 of the sleeve member 36 extends about the mating proximal end 14. As seen in FIG. 5, the mating distal end 16 of the tubular member 18 is then set (i.e., abutted) against the mating proximal end 14 of the deformable tip 12 to thereby form a butt joint 40. In this position, a second section 42 of the sleeve member 36 extends about the mating distal end 16 of the tubular member 18, and the portion 34 of the mandrel 32 that extends past the mating proximal end 14 of the deformable tip 12 is received within the mating distal end 16 of the tubular member 18.

As is apparent from FIGS. 3 and 4, at the start of the method of the present invention, the mating proximal end 14 of the deformable tip 12 has a first flat end edge 44 and the mating distal end 16 of the tubular member 18 has a second flat end edge 46. The sleeve member 36 and the mandrel 32 are sized to snugly receive or be snugly received, respectively, by the deformable tip 12 and tubular member 18.

Figure 7:
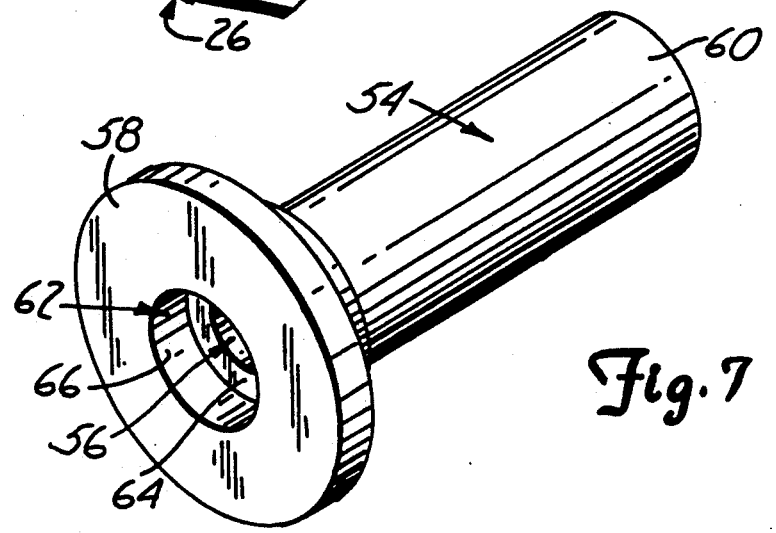
FIG. 7 is a perspective view showing the particulars of the pressure member shown in FIG. 6.

Next, as seen in FIG. 6, the combination of the tubular member 18, deformable tip 12, mandrel 32 and sleeve member 36 is inserted between the clamp members 48 of a clamping device 50 such that the tubular member 18 is positioned between the clamp members 48. A distal end 52 of the deformable tip 12 is received by a pressure member 54. As best seen in FIG. 7, the pressure member 54 includes a through opening 56 extending from a proximal end 58 to a distal end 60 of the pressure member 54. The proximal end 58 includes a pressure ledge 62 defined by a circular bottom wall 64 and a circumferential side wall 66. As seen in FIG. 6, the pressure ledge 62 is configured to receive the distal end 52 of the deformable tip 12, while the through opening 56 is configured to slidably receive a second portion 68 of the mandrel 32.

Next, as seen in FIG. 8, the clamp members 48 of the clamping device 50 are engaged with the tubular member 18 to secure the tubular member 18 against movement relative to the deformable tip 12. Heat (as represented by the wavy arrows 70) from a heat source 72 is applied to the deformable tip 12 and tubular member 18 to soften the mating proximal and distal ends 14 and 16 at the butt joint 40. Approximately two thirds of the heat from the heat source 72 is directed to the mating distal end 16 of the tubular member 18, while the remaining one third of the heat is directed to the mating proximal end 14 of the deformable tip 12. This is done because the material used to form the tubular member 18 is stiffer then the material used to form the deformable tip 12. Therefore, more heat is required to soften the mating distal end 16 of the tubular member 18 then is required to soften the mating proximal end 14 of the deformable tip 12.

While heat is applied to the butt joint 40, the deformable tip 12 is continuously forced against the tubular member 18 by way pressure exerted by the pressure member 54 (see FIG. 8). The pressure is exerted along a longitudinal axis 74 formed by the deformable tip 12 and tubular member 18. The pressure of the pressure member 54 maintains contact between the mating proximal end 14 of the deformable tip 12 and the mating distal end 16 of the tubular member 18. The heat from the heat source 72 and the pressure from the pressure member 54 act to soften the butt joint 40 and render the mating proximal end 14 of the deformable tip 12 and the mating distal end 16 of the tubular member 18 flowable.

Heat is applied to the butt joint 40 for a sufficient period of time to soften the butt joint 40. In one embodiment, the tubular member 18 and deformable tip 12 are both formed of polyether block amide and a radiopaque compound, except that the material of the deformable tip 12 has a lower durometer then the material of the tubular member 18. In other words, the tubular member 18 is stiffer than the deformable tip 12. In addition to the different durometers, the tubular member 18 also includes the coating of lubricous material 31 while the deformable tip 12 has no such coating. In one embodiment, the tubular member 18 has a durometer of 66 while the deformable tip 12 has a durometer of 37 and the butt joint 40 is heated by the heat source 72 for 45 seconds at a temperature 430° F. while the pressure member 54 maintains 10 p.s.i. of pressure against the distal end 52 of the deformable tip 12. The mandrel 32 and the sleeve member 44 prevent the mating proximal and distal ends 14 and 16 from bulging radially during softening of the butt joint 40.

After the butt joint 40 is sufficiently heated and while maintaining the heat and pressure, the tubular member 18, the deformable tip 12, the mandrel 32, the sleeve member 44, the clamping device 50, and the pressure member 54 are all oscillated (as represented by the double headed arrow 75) relative to the heat source 72 along the longitudinal axis 74 by a piston and cylinder device 76 (see FIG. 9). The longitudinal oscillation causes the softened mating proximal and distal ends 14 and 16 to flow into one another. In one embodiment, the tubular member 18 and the deformable tip 12 are oscillated for a period of three seconds. This procedure causes the formation of the lap joint tip bond 20 (see FIGS. 1 and 2) wherein the mating proximal end 14 of the deformable tip 12 forms the tapered apex 22 that extends proximally, the mating distal end 16 of the tubular member 18 forms the V-shaped groove 24 that widens distally, and the partial butt joint 26 is formed between the flat edge portion 28 and the flat edge section 30 at the coating of lubricous material 31.

After the oscillation, the clamping device 50 is disengaged from the tubular member 18, thereby releasing the tubular member 18, and the pressure member 54 is disengaged from the distal end 52 deformable tip 12, thereby removing the pressure at the deformable tip 12. The tubular member 18 with the deformable tip 12 coupled thereto is then removed from the heat source 72 and the lap joint tip bond 20 is allowed to solidify (i.e., cure) by cooling at room temperature. The heat source 72 remains on so that it is ready for the formation of subsequent lap joint tip bonds 20. When the lap joint tip bond 20 has solidified, formation of the guide catheter 10 is complete.

Figure 10:
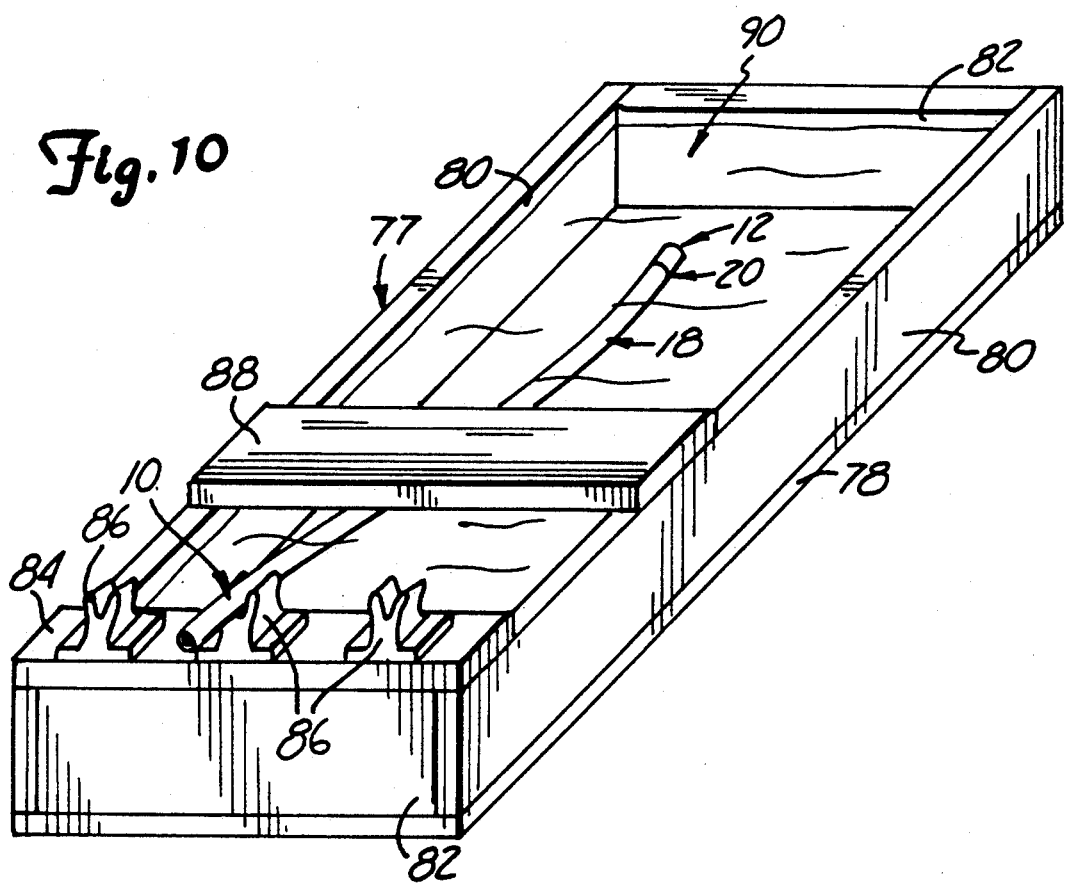
FIG. 10 is a perspective view of a cooling bath apparatus that may be used to increase the rate of curing of the lap joint tip bond formed by the method of the present invention.

Alternatively, solidification of the lap joint tip bond 20 can be hastened by immersing the lap joint tip bond 20 in a cooling bath 77 shown in FIG. 10. The cooling bath 77 includes a bottom wall 78, a pair of spaced, upstanding sidewalls 80 and a pair of spaced, upstanding end walls 82. A guide catheter support plate 84 is mounted to upper edges of the sidewalls 80 at a first end of the cooling bath 77. The support plate 84 carries a plurality of guide catheter supports 86. A dunking plate 88 is mounted to the upper edges of the sidewalls 80 spaced from the support plate 84.

The cooling bath 76 may be filled with a cooling substance such as an alcohol bath 90 which would hasten cooling of the lap joint tip bond 20 and thereby solidification of the lap joint tip bond 20 via evaporation of the alcohol bath 90. As seen in FIG. 10, a guide catheter 20 with a lap joint tip bond 20 to be cooled is placed across one of the guide catheter supports 86 and beneath the dunking plate 88 which serves to maintain the lap joint tip bond 20 immersed in the alcohol bath 90. The lap joint tip bond 20 is left in the alcohol bath 90 for a sufficient period of time to cool the lap joint tip bond 20.

Figure 11:
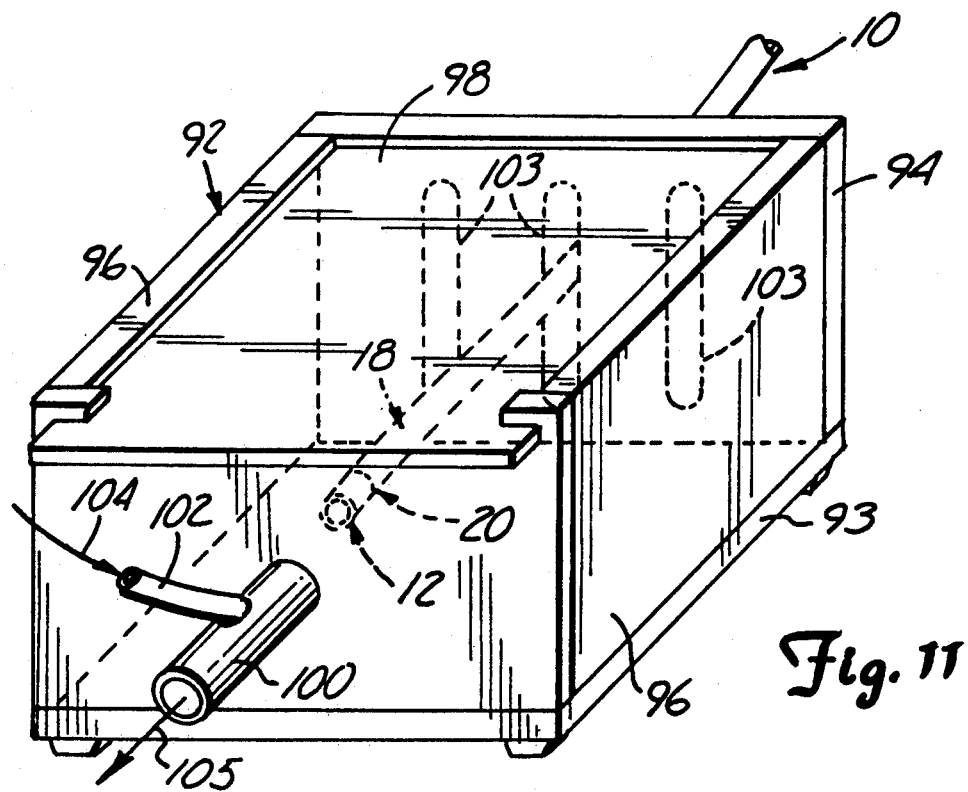
FIG. 11 is a perspective view of a circulating air cooler that may alternately be used to increase the rate of curing of the lap joint tip bond formed by the method of the present invention.

Solidification of the lap joint tip bond 20 can be alternatively hastened by the use of a circulating air cooler 92, such as a VORTEC cooler as shown in FIG. 11. The circulating air cooler 92 includes a bottom wall 93, a rear wall 94, a front wall 95, a pair of sidewalls 96 and a top wall 98. An air exhaust port 100 extends out through the front wall 95. An air inlet tube 102 extends through the exhaust port 100 and into the confines of the circulating air cooler 92. A guide catheter 10 with a lap joint tip bond 20 to be cooled is inserted into the cooler 92 through one of a plurality of slots 103 in the rear wall 94 such that the lap joint tip bond 20 is within the confines of the circulating air cooler 92. Air (as represented by the arrow 104) is forced into the confines of the circulating air cooler 92 through the air inlet tube 102. The air circulates within the cooler 92 and is exhausted through the exhaust port 100 (as represented by the arrow 105). The circulating air within the circulating air cooler 92 hastens cooling of the lap joint tip bond 20 and thereby solidification of the lap joint tip bond 20. The lap joint tip bond 20 is left in the circulating air cooler 92 for a sufficient period of time to cool the lap joint tip bond 20.

This method of forming a guide catheter 10 with a deformable tip 12 is relatively uncomplicated. The method of the present invention produces a high strength lap joint tip bond 20 exhibiting a large amount of surface area contact between the mating distal end 16 of the tubular member 18 and the mating proximal end 14 of the deformable tip 12 that make up the guide catheter 10. This large amount of surface area contact creates an extremely strong bond.

Although the present invention has been described with reference to preferred embodiments, workers skilled in the art will recognize that changes may be made in form and detail without departing from the spirit and scope of the invention.

What is claimed is:

1. A method of forming a guide catheter having a soft deformable tip on a distal end thereof, comprises the steps of:
    providing a tubular, deformable tip having a mating proximal end;
    providing a tubular member having a mating distal end, the tubular member being stiffer then the tubular, deformable tip;
    butting the mating proximal end of the deformable tip up against the mating distal end of the tubular member to form a butt joint;
    softening the butt joint to render the mating proximal end of the deformable tip and the mating distal end of the tubular member flowable;
    longitudinally oscillating both the deformable tip and tubular member such that the mating ends of the deformable tip and tubular member flow into one another to form a connection zone; and
    solidifying the connection zone to firmly couple the deformable tip to the tubular member, thereby forming a guide catheter having a soft deformable tip.

2. The method of claim 1 and further including the steps of:
    providing a mandrel adapted to be closely received within the tubular member and deformable tip;
    inserting the mandrel into the deformable tip such that a portion of the mandrel extends past the mating proximal end of the deformable tip;
    inserting the portion of the mandrel that extends past the mating proximal end of the deformable tip into the tubular member through the mating distal end thereof; and
    sliding one of the tubular member and deformable tip longitudinally along the mandrel so that the mating proximal end of the deformable tip contacts the mating distal end of the tubular member to form the butt joint.

3. The method of claim 2, and further including the steps of:
    providing a clamp adapted to closely receive one of the deformable tip and tubular member;
    securing one of the deformable tip and tubular member with the clamp; and
    continuously forcing the other one of the deformable tip and tubular member longitudinally along the mandrel into the one of the deformable tip and tubular member secured by the clamp, to maintain contact between the mating ends of the deformable tip and tubular member.

4. The method of claim 1 and further including the steps of:
    providing a sleeve adapted to closely receive the deformable tip and the tubular member; and
    generally centering the sleeve about the butt joint.

5. The method of claim 1 wherein the step of softening the butt joint further includes:
    providing a heat source; and
    heating the butt joint for a sufficient period of time with the heat source to render the proximal end of the deformable tip and the distal end of the tubular member flowable.

6. The method of claim 5 wherein heating the butt joint includes the step of:
    applying heat for approximately 45 seconds at a temperature of approximately 430° F.

7. The method of claim 1 wherein solidifying the connection zone includes the step of:
    placing the connection zone in an cooling bath to increase the rate of solidification of the connection zone.

8. The method of claim 1 wherein solidifying the connection zone includes the step of:
    placing the connection zone in a circulating air cooler to increase the rate of solidification of the connection zone.

9. The method of claim 3 wherein continuously forcing the other one of the deformable tip and tubular member longitudinally along the mandrel into the one of the deformable tip and tubular member secured by the clamp includes the step of:
    applying a longitudinal force of approximately 10 p.s.i. against the other one of the deformable tip and tubular member.

10. The method of claim 1 wherein longitudinally oscillating the deformable tip and tubular member such that the mating ends of the deformable tip and tubular member flow into one another to form a connection zone includes the step of:
    applying an oscillation force for approximately three seconds.

11. A method of forming a guide catheter having a soft deformable tip on a distal end thereof, comprises the steps of:
    providing a tubular, deformable tip having a mating proximal end;
    providing a tubular member having a mating distal end, the tubular member being stiffer then the tubular, deformable tip;
    inserting a mandrel into the deformable tip such that a portion of the mandrel extends past the mating proximal end of the deformable tip;
    sliding a sleeve over the deformable tip such that a first section of the sleeve extends about the mating proximal end of the deformable tip;
    butting the mating distal end of the tubular member against the mating proximal end of the deformable tip such that the mating distal end extends about the portion of the mandrel that extends past the deformable tip, and a second section of the sleeve extends about the mating distal end of the tubular member;
    securing the tubular member against movement relative to the deformable tip;
    heating the butt joint while continuously forcing the deformable tip longitudinally along the mandrel against the tubular member to render the mating proximal end of the deformable tip and the mating distal end of the tubular member flowable;

longitudinally oscillating both the deformable tip and tubular member such that the mating ends of the deformable tip and tubular member flow into one another to form a lap joint wherein the mating proximal end of the deformable tip forms a tapered apex that extends proximally, and wherein the mating distal end of the tubular member forms a V-shaped groove that widens distally; and solidifying the lap joint which firmly couples the deformable tip to the tubular member thereby forming a guide catheter with a soft deformable tip.

* * * * *